(12) United States Patent
Sarkar et al.

(10) Patent No.: US 9,028,893 B2
(45) Date of Patent: May 12, 2015

(54) **ANTITUBERCULOSIS COMPOSITION OF *BYTTNERIA* SPECIES**

(71) Applicant: Council of Scientific & Industrial Research, New Delhi (IN)

(72) Inventors: Dhiman Sarkar, Maharashtra (IN); Swati Pramod Joshi, Maharashtra (IN); Upasana Singh, Maharashtra (IN); Ketaki Dilip Shurpali, Maharashtra (IN); Roshan Rajan Kulkarni, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/624,103

(22) Filed: Sep. 21, 2012

(65) Prior Publication Data

US 2013/0040007 A1    Feb. 14, 2013

Related U.S. Application Data

(63) Continuation-in-part of application No. PCT/IB2011/000598, filed on Mar. 22, 2011.

(30) Foreign Application Priority Data

Mar. 22, 2010  (IN) .............................. 680/DEL/2010

(51) Int. Cl.
*A61K 36/185*    (2006.01)
*A61K 8/97*    (2006.01)

(52) U.S. Cl.
CPC .................................... *A61K 36/185* (2013.01)

(58) Field of Classification Search
CPC .................................................... C07K 14/415
USPC ........................................................ 424/779
See application file for complete search history.

(56) References Cited

U.S. PATENT DOCUMENTS

2008/0242676 A1* 10/2008 Arora et al. .............. 514/254.01
2009/0136923 A1*  5/2009 Park et al. ......................... 435/6

OTHER PUBLICATIONS

Honey Bee (Animal Husbandry, Indian Institute of Management, Honey Bee, vols. 1-12, 1990, p. VIII).*
B.A. Adeniyi et al., "In vitro anti-mycobacterial activities of three species of Cola plan extracts (Sterculiaceae)," Phytotherapy Research, vol. 17, No. 5, May 2004, p. 414-418.
F. Rahman et al., "Medicinal plants used against tuberculosis by traditional medicinal practitioners of Bogra district, Bangladesh," Planta Medica, vol. 75, No. 9, Jul. 2009, p. 960 (abstract).
B. Phetsuksiri et al., "Unique mechanism of action of the thiorea drug isoxyl on Mycobacterium tuberculosis," Journal of Biological Chemistry, vol. 278, No. 52, Dec. 2003, p. 53123-53130.
M.V. Tullius et al., "High extracellular levels of Mycobacterium tuberculosis glutamine synthetase and superoxide dismutase in actively growing cultures are due to high expression and extracellular stability rather than to a protein-specific export mechanism," Infection and Immunity, vol. 69, No. 10, Oct. 2001, p. 6348-6363.
U. Singh and D. Sarkar, "Development of a simple high-throughput screening protocol based on biosynthetic activity of Mycobacterium tuberculosis glutamine synthetase for the identification of novel inhibitors," Journal of Biomolecular Screening, vol. 11, No. 8, 2006, p. 1035-1042.
International Search Report for international application No. PCT/IB2011/000598, dated Jul. 21, 2011 (3 pages).

* cited by examiner

*Primary Examiner* — Chris R Tate
*Assistant Examiner* — Randall Winston
(74) *Attorney, Agent, or Firm* — Hamre, Schumann, Mueller & Larson, P.C.

(57) ABSTRACT

Active fractions exhibiting anti-tuberculous activity from the plant *Byttneria herbecea* (family—Sterculiaceae) are described. Methanol extracts of the aerial part of *Byttneria herbecea* exhibited activity against MtbGS in primary screening of biosynthetic assay. Subsequent fractionation was carried out in organic solvents. Out of all these, two fractions (fraction D and K) are exhibiting inhibitory activity against *M. tuberculosis* glutamine synthetase activity. These fractions D and K are inhibiting 74% and 44% respectively at 7.5 mg/ml concentrations. The determined $IC_{50}$ value of the fraction K is found to be 4.5 mg/ml from the dose response curve against the purified *Mycobacterium tuberculosis* Glutamine Synthetase. The $IC_{50}$ value for *M. bovis* BCG is 1.56 µg/ml. It was observed that there was no significant effect on proliferation of HL-60 cell line at 10×MIC levels of the hits. This data indicated that these compounds could be initially considered to be safe.

6 Claims, 5 Drawing Sheets

ANTITUBERCULOSIS COMPOSITION OF *BYTTNERIA* SPECIES

This application incorporates by reference WO 2011/117708 filed on Mar. 22, 2011 and Indian application 680/DEL/2010 filed on Mar. 22, 2010 in their entirety.

FIELD

This disclosure relates to a composition comprising an extract of *Byttneria* species for inhibiting *Mycobacterium tuberculosis* glutamine synthetase enzyme of bacterium *Mycobacterium tuberculosis* causing tuberculosis. More particularly, this disclosure relates to the anti tubercular activity of *Byttneria* species by inhibiting the enzyme MtbGS (*Mycobacterium tuberculosis* Glutamine Synthetase).

BACKGROUND

WHO estimated that 9.27 million new cases of TB occurred in the year 2007, in comparison to 9.24 million new cases in the year 2006. Of these 9.27 million new cases, an estimated 44% or 4.1 million (61 per 100 000 population) were new smear positive cases. India has more new TB cases annually than any other country. India is known to have the largest incidence of the disease in its population with up to 1.8 million affected. It is estimated that, in 2007, there were 1.37 million incidence of HIV-positive TB (14.8% of total cases) and 456 000 deaths from TB among HIV-positive people. The only global study done on this emerging threat found that nearly 20% of multi drug resistant tuberculosis (MDR-TB) cases in the hardest-hit regions were extremely/extensively drug resistant tuberculosis (XDR-TB). There is a need in the art to have molecules that can act against the bacilli effectively to reduce the incidence of tuberculosis and as well reduce morbidity and mortality due to the disease. Moreover, this can be a strategy to overcome multi drug resistant bacilli, which is increasingly making conventional treatment regimens ineffective.

The enzyme MtbGS (*Mycobacterium tuberculosis* Glutamine Synthetase) was identified as a target for the disease, and it plays an important role in cell wall biosynthesis, by synthesizing Poly-L-glutamate-glutamine complex. The extracellular localization of the GlnA1 enzyme from *M. tuberculosis*, *M. bovis* and other similar bacteria was associated with its involvement in the synthesis of a cell wall component poly(L-glutamic acid glutamine).

B. A. Adeniyi et al in an article titled "In vitro anti-mycobacterial activities of three species of *Cola* plant extracts (Sterculiaceae)" in Phytotherapy Research, Volume 18, Issue 5, Pages 414-418, published online: 26 May, 2004; discloses the screening of extracts obtained from three Nigerian Sterculiaceae plants: *Cola accuminata*, *C. nitida* and *C. milleni* for anti-mycobacterium properties using a slow growing *Mycobacterium bovis* ATCC 35738 at 1000 μg/ml using the radiometric (BACTEC) method. The extracts were also tested against six fast growing ATCC strains of *M. vaccae* using the broth microdilution method. The methanol extracts from both leaves, stem bark and root bark of *Cola accuminata* and from the leaves and stem bark of *C. nitida* and *C. milleni* were not active at the highest concentration of 1000 μg/ml. Only the methanol extract of root bark for both *C. nitida* and *C. milleni* were found to be potent against both *M. bovis* and strains of *M. vaccae*.

Tullius, M. V., G. Harth, and M. A. Horwitz. 2001. High extracellular levels of *Mycobacterium tuberculosis* glutamine synthetase and superoxide dismutase in actively growing cultures are due to high expression and extracellular stability rather than to a protein-specific export mechanism. Infect. Immun. 69:6348-6363.

SUMMARY

This disclosure describes a composition comprising an extract of *Byttneria* species. The extract is useful for inhibiting *Mycobacterium tuberculosis* glutamine synthetase enzyme of bacterium *Mycobacterium tuberculosis* causing tuberculosis.

This disclosure also describes an extract of plant *Byttneria*, inhibiting the activity of enzyme *Mycobacterium tuberculosis* glutamine synthetase (MtbGS) of bacterium *Mycobacterium tuberculosis* causing tuberculosis.

This disclosure also describes an anti-bacterial extract effective against *Mycobacterium tuberculosis*.

Further, this disclosure describes an extract of *Byttneria herbecea* that inhibits MtbGS and thus provides a method of treatment of tuberculosis.

One advantage is that the mode of action of the compound is known, which increases the potential of *Byttneria herbecea* for becoming an anti-tubercular herbal drug.

In one embodiment, a composition is provided comprising an extract of *Byttneria* species for inhibiting *Mycobacterium tuberculosis* glutamine synthetase enzyme of bacterium *Mycobacterium tuberculosis* causing tuberculosis. Further the disclosure relates to inhibition of *Mycobacterium tuberculosis* in both dormant and growing stages. The disclosure further relates to a method of treatment of tuberculosis by administering the patient chemically processed extract of *Byttneria* species.

Further the disclosure describes use of *Byttneria* as such, chemically processed to form extracts and the inhibitory effect of extracts, thus having activity against disease conditions, tuberculosis in particular, in both dormant and growing stages of *Mycobacterium*.

In one embodiment, the purified fractions of the extracts are inhibitory against MtbGS.

In another embodiment, *Byttneria* plant parts as such are inhibitory against MtbGS.

In yet another embodiment the *Byttneria* plant, plant parts, extracts and their fractions are effective against mycobacterium tuberculosis in both growing and dormant phases.

In one more embodiment, *Byttneria* plant, plant parts, extracts and their fractions are useful for treatment of disease conditions.

In another embodiment, *Byttneria* plant, plant parts, extracts and their fractions are useful for treatment against disease conditions wherein *Byttneria* inhibits MtbGS.

In yet another embodiment a composition is provided comprising at least 3 μg/ml of an extract of *Byttneria* species for inhibiting *Mycobacterium tuberculosis* glutamine synthetase enzyme.

In a further embodiment the composition is useful for the treatment of tuberculosis.

In one embodiment the extract is effective against tuberculosis caused by *Mycobacterium* both in growth and dormant phases of bacilli.

In one embodiment the extract is used to prepare pharmaceutical composition and dosage forms for treating tuberculosis.

In one embodiment *Byttneria* species used is *Byttneria herbecea*.

This TLC was done to check the purity of the major component obtained after PLC. For this, Methanol:Chloroform (5:95) was used as developing phase.

Figure 4:
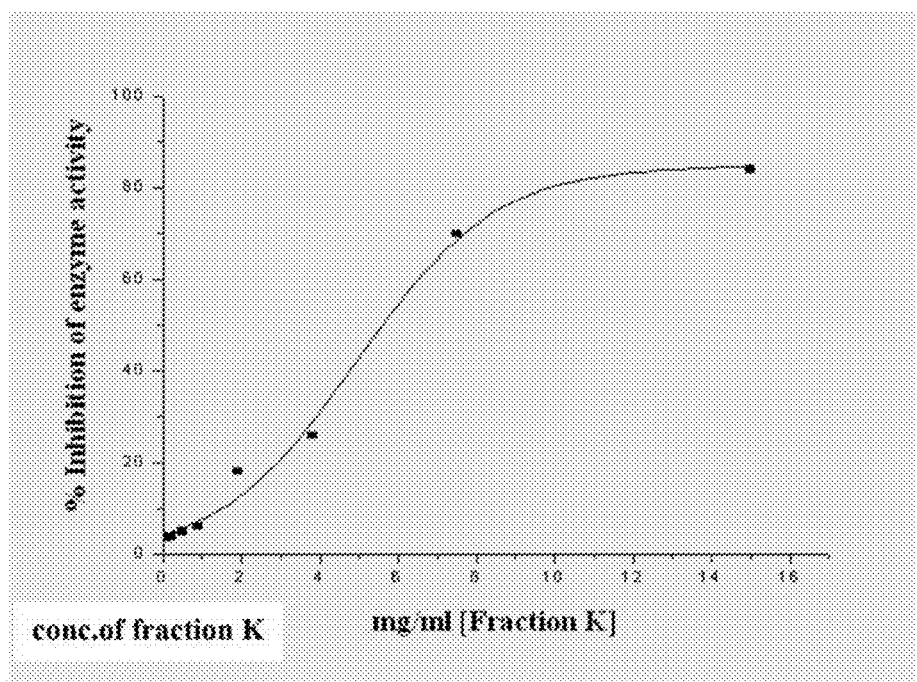

FIG. 4—Dose response curve was determined for fraction K on biosynthetic activity of purified *Mycobacterium tuberculosis* Glutamine Synthetase. The $IC_{50}$ value was determined using varied concentration of fraction K from 0.23-15 mg/ml. The determined $IC_{50}$ value is 4.5 mg/ml.

Figure 5:
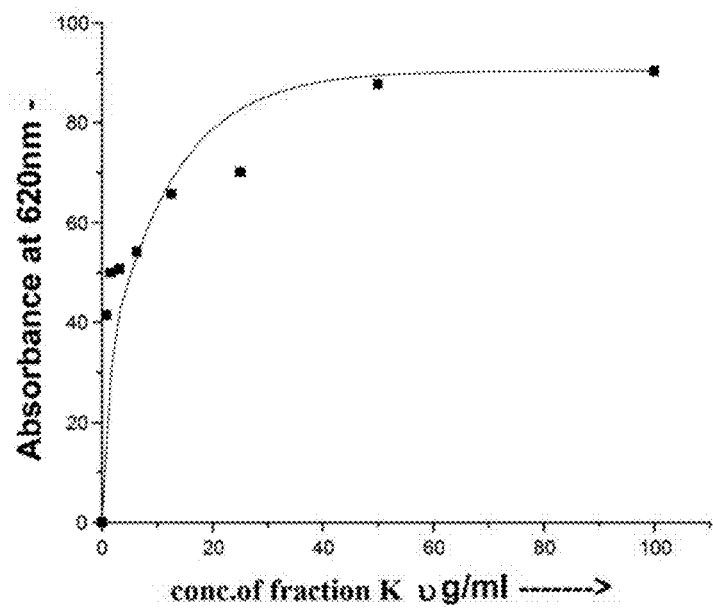

FIG. 5—The compounds of the invention were tested for their activity in the growth phase of the bacilli. The $IC_{50}$ value was determined using varied concentration of fraction K from 0.78-100 g/ml. The determined $IC_{50}$ value is 1.56 µg/ml.

DETAILED DESCRIPTION

Plants are collected under network project in September 2002 from Assam, The aerial parts i.e. Twigs of the *Byttneria* plant (Family Sterculiaceae, Genus: *Byttneria*, species—*herbecea*) are collected. Extract of the aerial parts of the *Byttneria* plant in solvents selected from aqueous and non-aqueous solvents, water, ethanol, chloroform, alone or combinations thereof are prepared and evaluated for inhibitory activity against MtbGS as exemplified herein in example 1. The extracts are characterized for their constituents and purified by well known techniques in the art.

The constituents of the *Byttneria* plant, plant parts, extracts and their fractions and further purified fractions are identified and evaluated for inhibitory effect of MtbGS. With reference to FIG. 5, wherein the $IC_{50}$ value is determined to be 1.56 µg/ml, the minimum inhibitory concentration (MIC) of the extract is determined to be two times the IC50 value ie the MIC is at least 3 µg/ml.

In an embodiment, a pharmaceutical composition comprising at least 3 µg/ml of the extract *Byttneria* plant parts is useful for the inhibition of MtbGS.

The pharmaceutical composition described herein is useful for the treatment of conditions wherein inhibition of MtbGS is required.

In an embodiment, the pharmaceutical composition is useful for treatment of tuberculosis. In another embodiment, the composition is useful for the treatment of tuberculosis in the growing as well as dormant phases of the tuberculosis causing organisms.

The pharmaceutical composition comprises the extract of *Byttneria* plant parts and pharmaceutically acceptable ingredients selected from, but not limited to fillers, binders, flavours, disintegrants, lubricants, dissolution rate controlling agents, sweeteners, vehicles and such like. The composition may optionally be in conventional dosage form or optionally as sustained, timed, controlled or pulsatile release forms.

In an embodiment, a method of treatment of tuberculosis by administering a subject the extract of *Byttneria* plant is provided.

In another embodiment, a method of treatment of tuberculosis by administering a subject the composition comprising extract of *Byttneria* plant is provided.

In yet another embodiment, a method of inhibiting MtbGS using the composition comprising extract of *Byttneria* plant is provided.

In yet another embodiment, a method of inhibiting MtbGS using extract of *Byttneria* plant is provided.

In one more embodiment, use of the extract of *Byttneria* plant for preparing pharmaceutical composition for inhibiting MtbGS and/or for treating tuberculosis is provided.

In another embodiment, use of the extract of *Byttneria* plant for inhibiting MtbGS and/or for treating tuberculosis is provided.

In yet another embodiment, use of the composition comprising extract of *Byttneria* plant for inhibiting MtbGS and/or for treating tuberculosis is provided.

The embodiments described herein are further illustrated by the examples given herein below which should not however be construed to limit the scope of the claimed invention.

EXAMPLES

Example 1

Protocol for Identification of MtbGS Inhibitors

The assay mix contains 50 mM HEPES (4-(2-hydroxyethyl)-1-piperazineethanesulfonic acid), buffer pH 6.8, 220 mM L-glutamic acid (pH adjusted to 6.8), 7.5 mM Ammonium chloride, 32.5 mM Magnesium chloride, and 62.5 µg/ml enzyme (*Mycobacterium tuberculosis* Glutamine Synthetase). 85 µl of the reaction mix is added with 5 µl of sample (*Byttneria* extract). In the control 5 µl of DMSO (Dimethyl sulfoxide) is added and 5 µl of 420 mM EDTA (ethylenediaminetetraacetic acid) is added in the blank. The reaction is started by adding 7.6 mM ATP (pH adjusted ~6.8) in the reaction mixture and incubated for 2 h at 25° C. The reaction is terminated by adding stop reagent followed by addition of citrate to block the further hydrolysis of ATP. The whole mixture is kept at room temperature for another 30 min to read the color at 655 nm by spectramax plate reader. The methanol extract of *Byttneria* Spp. is found active against MtbG).

[Ref—Singh. U, Sarkar. D., Development of a Simple High-Throughput Screening Protocol Based on Biosynthetic Activity of *Mycobacterium tuberculosis* Glutamine Synthetase for the Identification of Novel Inhibitors, Journal of Biomolecular Screening 11(8); 2006.]

Example 2

Column Chromatography of Methanol Extract of Example 1

19 gms of the sample is chromatographed by 200 gms of silica gel (100-200 mesh) using mobile phase gradient as per table-1. 25 Fractions are collected during this stage. TLC of all these collected fractions is carried out using 5:95 MeOH:CHCl$_3$ developing phase on alumina coated silica gel TLC plates to check the purity. Fractions showing similar TLC (FIG. I) pattern are pooled and taken in 15 ml glass test tubes to obtain 11 fraction (A, B, C, D, E, F, G, H, I, J, K). After removal of solvent these fractions are evaluated for their bioactivity using the protocol mentioned in example 1. Fraction D (4$^{th}$ fraction) and K (11$^{th}$ fraction) a found to exhibit activity against MtbGS.

TABLE I

| Steps | Choloform % | Methanol % | Water % | Volume ml |
|---|---|---|---|---|
| 1. | 98 | 2 | — | 1000 |
| 2. | 95 | 5 | — | 1000 |
| 3. | 90 | 10 | — | 1000 |
| 4. | 85 | 15 | — | 1000 |
| 5. | 80 | 20 | — | 1000 |
| 6. | — | 100 | — | 1000 |
| 7. | — | 50 | 50 | 500 |

Example 3

Purification of the Fraction D (4th Fraction)

Figure 1:
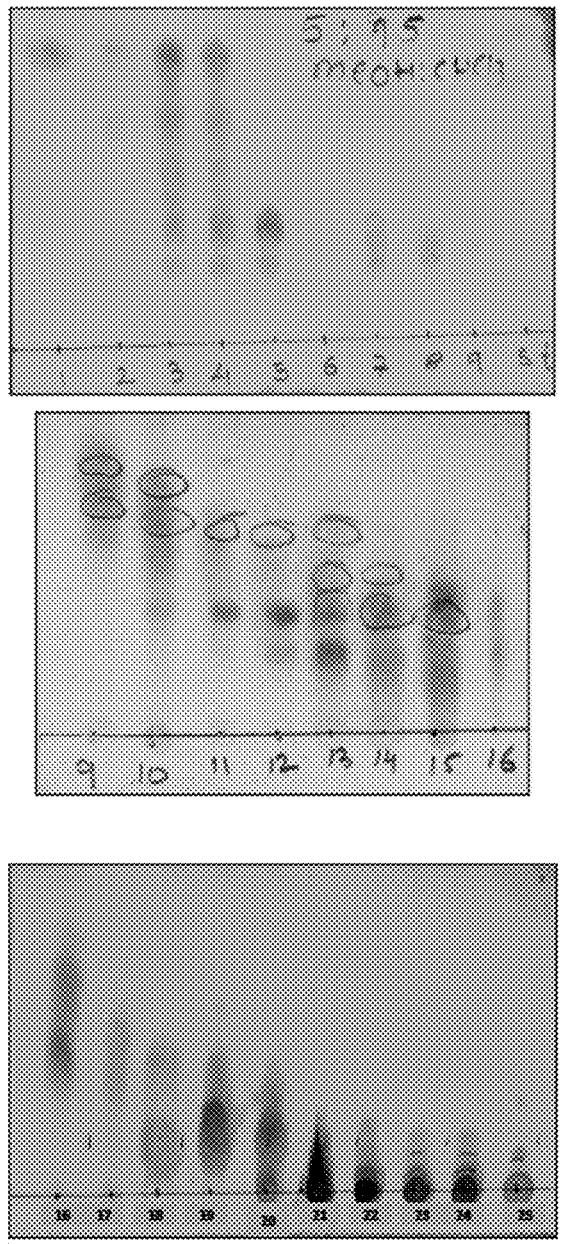
FIG. 1—TLC of 25 fractions collected from column chromatography. 5:95 MeOH:CHCl$_3$ was used as developing system for fractions collected from the column chromatography. Fractions showing similar TLC pattern of compounds were combined to obtain 11 fractions.
Figure 2:
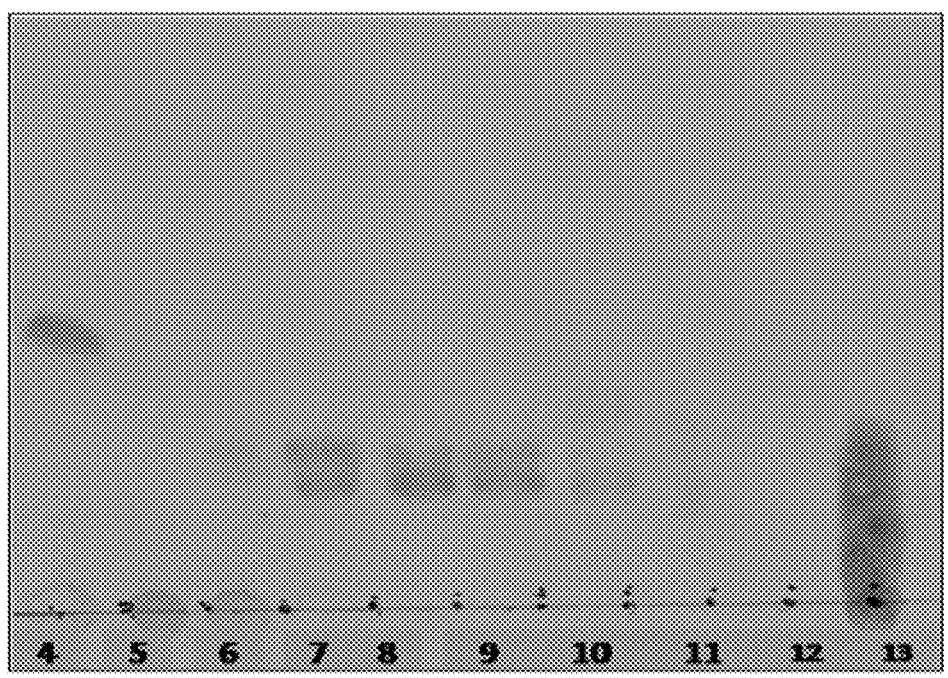
FIG. 2—TLC of pooled subfractions of Fraction D. 10:3:87 Acetonitrile:Methanol:Chloroform was used as developing system for these subfractions collected after carrying out the Column chromatography of fraction D. Fractions showing similar TLC pattern of compounds were combined and the final TLC was carried out.
Figure 3:
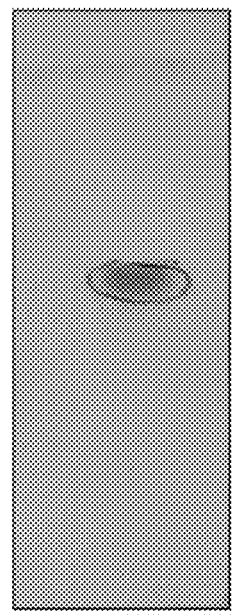
FIG. 3—TLC of major component of Fraction D4 obtained from preparative TLC (PLC)

100 mg of Fraction D is re-chromatographed by using 36 gms of Silica gel (100-200 mesh) and mobile phase as described in the table II. TLC of all the collected fractions is carried out (FIG. 2). After analyzing the TLC plates, the fractions are pooled into 10 final fractions D1-D10. Assay as in example 1 is carried out to identify the active fraction(s). The fraction D4 is found active.

TABLE II

| Step | Acetonitrile % | Methanol % | Chloroform % | Acetone % | Volume in ml |
|---|---|---|---|---|---|
| 1. | 10 | 1 | 89 | — | 200 |
| 2. | 10 | 2 | 88 | — | 200 |
| 3. | — | — | — | 100 | 100 |

Example 4

Purification of the Fraction K (11th Fraction)

9 gms of fraction K is separated by using RP $C_4$ column with Methanol:Water (50:50) as mobile phase. Band with major compound are taken out and extracted using 100% methanol. Solvent is evaporated and fractions K1-K25 are evaluated for bioactivity. Fractions K1-K19 are found active against MtbGS. Fraction K1 and K19 is further separated by using RP $C_{18}$ column using mobile phase as described in table III and the purity is assessed by RP $C_{18}$ Glass TLC plates. Structure of the active compound is identified by applying standard techniques.

TABLE (III)

| Steps | Methanol (% or ml)ml | Water (% or ml)ml | Volume (in ml) |
|---|---|---|---|
| 1. | — | 100 | 100 |
| 2. | 10 | 90 | 100 |
| 3. | 20 | 80 | 100 |
| 4. | 30 | 70 | 100 |
| 5. | 40 | 60 | 100 |
| 6. | 60 | 40 | 100 |
| 7. | 70 | 30 | 100 |
| 8. | 80 | 20 | 100 |
| 9. | 90 | 10 | 100 |
| 10. | 100 | — | 200 |

Example-5

Inhibition is determined against biosynthetic reaction catalyzed by MtbGS, using the optimized method mentioned above (Singh. U, Sarkar. D., Development of a Simple High-Throughput Screening Protocol Based on Biosynthetic Activity of *Mycobacterium tuberculosis* Glutamine Synthetase for the Identification of Novel Inhibitors, Journal of Biomolecular Screening 11(8); 2006) (Table-IV). Dose-response effect of fraction K on biosynthetic activity of MtbGS is determined by applying varying concentration of fraction K from 0.25 mg/ml-15 mg/ml. The determined $IC_{50}$ value from the dose response curve is 4.5 mg/ml (FIG. IV)

[Ref—Singh. U, Sarkar. D., Development of a Simple High-Throughput Screening Protocol Based on Biosynthetic Activity of *Mycobacterium tuberculosis* Glutamine Synthetase for the Identification of Novel Inhibitors, Journal of Biomolecular Screening 11(8); 2006.

TABLE (IV)

| Srl. no | Fractions | % Inhibition found on enzyme *M. tb* Glutamine synthetase | |
|---|---|---|---|
| | | 7.5 mg/ml | 15 mg/ml |
| 1 | Original MeoH Extract | 37% | 71% |
| 2 | 1st fractionation | Fraction D 74.2%  Fraction K 44.5% | Fraction D 100%  Fraction K 80.63% |

Example-6

A protocol, which can identify inhibitors of active tubercle bacilli, is used to screen the compounds. Briefly, absorbance of the culture at 620 nm was used to represent the actively growing stage of the bacilli in this screening protocol. 2.5 µl of compound solution with varied concentration from 0.78-100 µg/ml of the sample in DMSO is aseptically transferred to individual wells of sterile 96-well plates. 247.5 µl of *M. bovis* BCG culture containing ~$10^5$ cells/ml, supplemented with L-Glutamic acid as nitrogen source in *M. pheli* medium, is aseptically transferred to each well to make up the total volume to 250 µl and the plate is covered with a sealer. 125 µl space is left in each well to make the headspace to culture volume ratio exactly 0.5. After sealing, these culture plates are incubated at 37° C. in an incubator. After 8 days of incubation, culture OD is read at 620 nm. The determined $IC_{50}$ value from the dose response curve is 1.56 µg/ml (FIG. V).

Advantages include but are not limited to:
1. A biological source for inhibiting MtbGS is provided
2. The extract of the invention inhibits *Mycobacterium* in both growth as well as dormant phases
3. The extract is useful in multi drug resistant as well as extremely/extensively drug resistant tuberculosis

We claim:

1. A composition for inhibiting *Mycobacterium tuberculosis* glutamine synthetase enzyme and/or for treating tuberculosis comprising an effective amount of an extract obtained from a twig of a *Byttneria* species, wherein the extract is obtained by extracting the twig of the *Byttneria* species with a solvent, the *Byttneria* species being *Byttneria herbacea*, wherein the solvent includes 1-100% methanol, 80-98% chloroform or a mixture thereof, and wherein the composition comprises at least 3 µg/ml of said extract.

2. The composition as claimed in claim 1, further comprising a pharmaceutically acceptable carrier, wherein the composition comprises the extract in an amount sufficient for inhibiting *Mycobacterium tuberculosis* glutamine synthetase enzyme.

3. The composition as claimed in claim 1, wherein said composition comprises the extract in an amount sufficient for the treatment of tuberculosis.

4. The composition as claimed in claim 1, wherein the amount of the extract is sufficient to be effective against tuberculosis caused by *Mycobacterium* both in growth and dormant phases of bacilli.

5. The composition as claimed in claim 1, wherein the composition is a pharmaceutical dosage form that is selected from a sustained, timed, controlled and pulsatile release form.

6. A method of treating tuberculosis comprising administering an effective amount of the composition of claim 1 to a subject in need thereof.

* * * * *